United States Patent
Wagner et al.

(10) Patent No.: US 6,512,139 B1
(45) Date of Patent: Jan. 28, 2003

(54) OXIDATION INHIBITORS IN PROSTANE DERIVATIVES

(75) Inventors: Torsten Wagner, Berlin (DE); Martin Wessel, Berlin (DE); Ralph Lipp, Berlin (DE); Bernd Iffert, Berlin (DE); Heinrich Michel, Berlin (DE); Jürgen Westermann, Berlin (DE); Helmut Dahl, Berlin (DE); Werner Skuballa, Berlin (DE)

(73) Assignee: Schering Aktiengesellschaft (DE)

( * ) Notice: Subject to any disclaimer, the term of this patent is extended or adjusted under 35 U.S.C. 154(b) by 0 days.

(21) Appl. No.: 09/720,134

(22) PCT Filed: Jun. 22, 1999

(86) PCT No.: PCT/EP99/04278

§ 371 (c)(1),
(2), (4) Date: Mar. 7, 2001

(87) PCT Pub. No.: WO99/67212

PCT Pub. Date: Dec. 29, 1999

(30) Foreign Application Priority Data

Jun. 22, 1998 (DE) .......................... 198 28 881

(51) Int. Cl.[7] ..................... C07C 405/00; A61K 31/557
(52) U.S. Cl. ..................... 562/503; 560/121; 546/322; 514/573
(58) Field of Search .................. 514/573; 560/121; 562/503; 546/322

(56) References Cited

U.S. PATENT DOCUMENTS 5,654,339 A * 8/1997 Scholz ..................... 514/573

FOREIGN PATENT DOCUMENTS

| DE | 3816801  | 11/1989   |
| EP | 055208   | 6/1982    |
| EP | 369463   | 5/1990    |
| JP | 11322612 | * 11/1999 |
| WO | 8705294  | 9/1987    |
| WO | 8807037  | 9/1988    |
| WO | 9943303  | 9/1990    |

OTHER PUBLICATIONS

Steiner T. et al: "A side chain of diastereomeric iloprost protudes from the cage in the complex . . . " *Carbohydrate Research*, vol. 192. 1989, pp. 43–49.

* cited by examiner

*Primary Examiner*—Samuel Barts
*Assistant Examiner*—Devesh Khare
(74) *Attorney, Agent, or Firm*—Millen, White, Zelano & Branigan, P.C.

(57) ABSTRACT

The invention relates to the use of an oxidation inhibitor, i.e. active carbon, for ambient air in industrial manufacturing, especially in the processing of prostane derivatives, whereby the oxidation inhibitor removes ozone from the process air before contact with said prostane derivatives. The concentration of decomposition products is reduced.

29 Claims, No Drawings

OXIDATION INHIBITORS IN PROSTANE DERIVATIVES

The invention relates to the use of an oxidation inhibitor for the ambient air in industrial manufacturing, especially in the processing of prostane derivatives, in this case preferably during the wet phase.

PRIOR ART

The active ingredient "iloprost-β-cyclodextrin" bears the systematic designation 5-(E)-(1S,5S,6R)-7-hydroxy-6[(E)-(3S,4RS)-3-hydroxy-4-methyl-1-octen-6-inyl]bicyclo[3.3.0]-octen-3-ylidene pentanoic acid as a β-cyclodextrin inclusion compound. The active ingredient is manufactured in the form of crude pellets by the following steps.

(i) Mixing of the active ingredient iloprost-β-cyclodextrin and the adjuvants lactose and avicel, (ii) Pelletization with about 20.5% water,
   high-speed mixing,
   extruding and
   spheronization, (iii) Drying in a fluidized-bed dryer,
   filling and
   drying.

The individual steps are described in detail in the following literature: H. SUCKER, P. FUCHS, and P. SPEISER: Pharmazeutische Technologie [Pharmaceutical Technology], Georg Thieme Verlag, Stuttgart, N.Y., 2nd Edition, 1991.

It should be noted that the pelletization in step (ii) is carried out intermittently, i.e., the active-ingredient-containing powder mixture with 0.1% iloprost is processed in cycles in about 5 kg portions. The moist crude pellet cycles are first collected in succession in a fluidized-bed dryer. After the last cycle in the dryer takes place, the final drying begins.

In the above-mentioned production process, methanediol-ketone contamination occasionally occurred in addition to the pure iloprost. This corresponds to the nomenclature with the name (1S,2R,3R,5R)-3-hydroxy-2-[(E)-(3S,4RS)-3-hydroxy-4-methyl-1-octen-6-inyl-bicyclo[3.3.0]octan-7-one. In this case, this is a decomposition product that is produced by oxidation. In the case of an occurrence, various parameters were important for the amount of decomposition product. In the wet state, the oxidation depended on the water content and the incubation time. It was seen that the temperature can play a role. It was also obvious that the active ingredient was sensitive to the mixture with avicel and lactose, but not to the active ingredient by itself. Although the same parameters were maintained, different amounts of decomposition product, which occasionally was allowed below the detection limit of <0.1%, were produced. Thus, occasionally values of between 0.6% to 4% were used. As a result, the purity requirements were not always met.

OBJECT AND ACHIEVEMENT

The object is thus to offer oxidation protection in the production, especially in the processing of prostane derivatives, whereby the oxidation products are avoided or are considerably reduced in their concentration.

The object is achieved by using an oxidation inhibitor for the ambient air in the case of industrial manufacturing, especially in the processing of prostane derivatives, whereby the oxidation inhibitor removes ozone from the process air before making contact with the prostane derivatives.

Oxidation Inhibitors

The oxidation inhibitor can be
an inert gas atmosphere,
a closed circuit that consists of synthetic air,
a metal catalyst,
an irradiation device with ultraviolet light,
a heating device with temperatures of at least 250° C. and a cooling device of the process air, or
an activated-carbon filter, through which the process air flows.

Combinations that consist of oxidation inhibitors are also possible.

The oxidation inhibitors are characterized as follows:

An inert gas atmosphere can consist of a nitrogen atmosphere or else a noble gas.

Synthetic air is run as a circuit, whereby the water that accumulates during drying must be removed. In this case, the composition of the process air can essentially correspond to the atmospheric air with the exception of ozone.

Platinum, copper or magnesium oxide may be metal catalysts.

Irradiation with ultraviolet light is preferably carried out at 254 nm.

The process air is heated preferably to 300° C. in the heating device. In this case, this air must then again be cooled in the cooling device. Both processes are preferably carried out in a heat exchanger.

Advantages

The different amounts of decomposition product with otherwise identical parameters were randomly determined as a function of the ozone content in the outside air. In this case, it can be noted that a monitoring of the ozone concentration in the pharmaceutical range is uncommon. Such monitoring has still not been described. A complicating factor is the fact that the decomposition products only occur if a threshold value of about 20 $\mu g$ of ozone/m$^3$ of ambient air is exceeded in the production. Consequently, no clear connection between the ozone concentration and the outside air was to be seen, so that a technical solution, which can suppress the decomposition products satisfactorily, was unlikely.

State of the Prostane Derivatives

Use of an oxidation inhibitor is preferred, whereby the prostane derivatives are mixed with cyclodextrin.

It has been shown that the oxidation occurs to an increased extent if the prostane derivatives are mixed with cyclodextrin. It is known, however, that specifically the complexes that consist of prostane derivatives and cyclodextrin are especially stable relative to an oxidation. Here, an otherwise common principle is thus violated.

The use of an oxidation inhibitor is preferred, whereby the prostane derivatives are found in a wet phase.

The presence of water results in an increased oxidation. Specifically in this case, oxidation proceeds more vigorously. As a result, the handling of the entire process is made more difficult, however. The moisture in the prostane derivatives and preferably in the complexes that consist of prostane derivatives and cyclodextrin must be removed. In this respect, cold traps or other devices are necessary to remove the water vapor from the process air.

Preferred is an activated-carbon filter with the following properties: (i) short contact times, (ii) minimum possible pressure drop through the filter, (iii) activated carbon has hydrophobic properties, and (iv) the filters have long service lives.

Prostane Derivatives

Preferred are prostane derivatives of general formula I or formula II

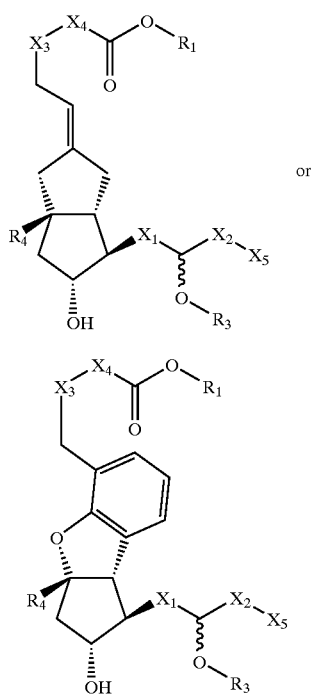

Formula I or

Formula II in which
- $X_1$ is a —$CH_2$—$CH_2$—; trans —CH=CH— or —C≡C—,
- $X_2$ is a straight-chain or branched, saturated alkylene group with 1 to 6 carbon atoms,
- $X_3$ is an —O— or —$CH_2$—,
- $X_4$ is a —$CH_2$— or —$[CH_2]_3$—,
- $X_5$ is an —H or —C≡C—$R_2$,
- $R_1$ is a hydrogen atom, an alkyl group with 1 to 6 carbon atoms, a cycloalkyl group with 5 or 6 carbon atoms or phenyl group,
- $R_2$ is a straight-chain or branched-chain, saturated or unsaturated alkyl group with 1 to 6 carbon atoms,
- $R_3$ is a hydrogen atom, an acyl radical with 1 to 4 carbon atoms or a benzoyl radical, and
- $R_4$ is an —H or —$CH_3$;
- whereby the —O—$R_3$ group is in α- or β-position, and their salts with physiologically compatible bases, if $R_1$ has the meaning of a hydrogen atom.

$X_2$ stands for straight-chain or branched, saturated alkylene groups with 1 to 6 carbon atoms, thus, for example, methylene, ethylene, propylene, isopropylene, whereby the methyl group is connected to the first or second carbon atom of ethylene, calculated from group A; butylene, methylpropylene, ethylethylene, dimethylethylene, whereby the methyl or ethyl group is connected arbitrarily to the alkylene chain; pentyl, methylbutylene, dimethylpropylene, ethylpropylene, methylethylethylene, whereby the methyl or ethyl groups are connected arbitrarily to the alkylene chain; hexylene, methylpentylene, dimethylbutylene, methylethylpropylene, whereby the methyl or ethyl group is connected arbitrarily to the alkylene chain.

Alkyl group $R_1$ comprises straight or branched alkyl groups with 1 to 6 carbon atoms, such as, for example, methyl, ethyl, propyl, butyl, isobutyl, tert-butyl, pentyl, neopentyl or hexyl.

Cycloalkyl group $R_1$ can contain 5 or 6 carbon atoms in the ring.

Alkyl group $R_2$ can consist of straight-chain or branched-chain, saturated or unsaturated alkyl radicals with 1 to 6 carbon atoms, and the alkyl radicals are preferably saturated. For example, methyl, ethyl, propyl, butyl, isobutyl, tert-butyl, pentyl, hexyl, butenyl, isobutenyl, propenyl, pentenyl or hexenyl groups can be mentioned.

Acyl group $R_3$ can consist of a straight-chain or branched-chain acyl group with 1 to 4 carbon atoms, such as, for example, acetyl, propionyl, butyryl or isobutyryl.

For salt formation with the free acids, inorganic and organic bases are suitable, as they are known to one skilled in the art for the formation of physiologically compatible salts. For example, there can be mentioned: alkali hydroxides, such as sodium and potassium hydroxide, alkaline-earth hydroxides, such as calcium hydroxide, ammonia, amines, such as ethanolamine, diethanolamine, triethanolamine, N-methylglucamine, morpholine, tris-(hydroxymethyl)-methylamine, etc. The β-cyclodextrin clathrate formation is carried out according to EP 0 259 468.

The prostane derivative 5-(E)-(1S,5S,6R)-7-hydroxy-6 [(E)-(3S,4RS)-3-hydroxy-4-methyl-1-octen-6-inyl]bicyclo [3.3.0]octen-3-ylidene pentanoic acid is preferred. Most preferred is the above-mentioned compound as a β-cyclodextrin inclusion compound.

Preferred is the use up to an ozone concentration of 20 μg/m³ in the ambient air during production. The outside air is not decisive by itself. During the suctioning of air from the outside air, ozone is catabolized, which is carried out solely by making contact with solid objects.

Advantages of the Activated-Carbon Filter

It was not logical and obvious to select activated carbon as oxidation protection, as the otherwise not so successful attempts to reduce the ozone content showed.

As a first solution, a nitrogen atmosphere was proposed, which, however, for technical reasons still contains residual amounts of oxygen, i.e., also ozone with respect to portions. The solution was not satisfactory. Further removal of oxygen would have been very costly in this situation. Moreover, the nitrogen atmosphere can only reasonably be implemented in an ambient air operation. In this case, because of the recycling of the air, an increased risk of cross-contamination exists.

As a second solution, it was proposed to operate the unit by itself with synthetic air in a circuit. In this case, the solution would also be very costly. As already depicted above, in this case the danger exists that a cross-contamination would occur.

As a third solution, metal catalysts that consist of platinum, copper or manganese oxide were used. The experts have given advice to this effect. The ozone reduction was not satisfactory, however. Also, in this case, a costly solution would have had to be adopted. Moreover, the use of supplied metal catalysts is connected to a high pressure loss. This has a negative effect on the filling of the dryer owing to the displacement of the pressure potential in the unit.

As a fourth solution, an irradiation with ultraviolet light was proposed. In this case, the danger exists that additional oxygen radicals are produced, which then must also be removed. This solution also turned out to be uneconomical.

In a fifth solution, air was heated to 300° C. In this case, ozone is thermally decomposed. It is unfavorable that the air must be cooled again to have a temperature of about 40° C. and less. It is disadvantageous that in the ventilation center, the necessary space required for the assemblies is not available.

The preferred solution with activated-carbon filters was not obvious, since the experts advised against using activated carbon, since the pressure drop through the activated-carbon filter was estimated as being too high. In this case, it is important to indicate that the air is suctioned, not pressed through the fluidized-bed dryer. The ventilator or the turbine is thus ruled out as a contamination source. In addition, these filters tend toward the abrasion of carbon particles that can get into the product bed. In addition, it must be calculated over longer service lives by the entering wet outside air with microbial contamination.

Nevertheless, this solution represents the best operating solution.

Process for the Production of Prostane Derivatives

In addition, the invention comprises a process for the production, especially processing, of medications that contain prostane derivatives, with use according to the invention of an oxidation inhibitor, comprising the following steps:
(i) Mixing of the active ingredient prostane-derivative-cyclodextrin and the adjuvants lactose and avicel,
(ii) Pelletization with water, preferably with 15 to 25% water, more preferably with 20–21% water,
high-speed mixing,
extruding and
spheronization,
(iii) Drying in a fluidized-bed dryer,
filling and
drying.

Preferred is a process for the production of medications that contain prostane derivatives with use according to the invention of an oxidation inhibitor, comprising the following steps:
(i) Mixing of the active ingredient iloprost-β-cyclodextrin, which bears the systematic designation 5-(E)-(1S,5S,6R)-7-hydroxy-6[(E)-(3S,4RS)-3-hydroxy-4-methyl-1-octen-6-inyl]bicyclo[3.3.0]octen-3-ylidene pentanoic acid, and the adjuvants lactose and avicel,
(ii) Pelletization with water, preferably with 15 to 25% water, more preferably with 20–21% water,
high-speed mixing,
extruding and
spheronization,
(iii) Drying in a fluidized-bed dryer,
filling and
drying.

EXAMPLE

The superiority of the invention is confirmed by examples. In this case, test preparations are implemented with and without activated-carbon filters. To test the action of the technical solution, a process air with an ozone content of 350±25 µg/m$^3$ is produced artificially, which, on the one hand, reaches the active ingredient directly, and, on the other hand, moves along the passage through an activated-carbon filter. In this case, an amount of air of 0.8 m$^3$/sec is conveyed through the filter.

If no filter is used, the process air in the contact area with the active ingredient has a content of 350±25 µg of ozone/m$^3$ of air. In this case, 5% decomposition products (w/w) are produced.

If an activated-carbon filter with the following properties is used, the ozone content is reduced to 8±0.5 µg of ozone/m$^3$ of air in the contact area with the active ingredient. Properties of the activated-carbon filter: (i) short contact times, (ii) minimum possible pressure drop through the filter, (iii) activated carbon has hydrophobic properties, and (iv) the filters have long service lives.

The filter is a standard activated-carbon filter, pressed from cylindrical shaped bodies with a diameter of about 3 mm, which are used as filter cartridges. As a result, 0.1% and less decomposition products (w/w) are produced. Such an amount of decomposition products is pharmacologically harmless.

At this time according to this process, the active ingredient 5-(E)-(1S,5S,6R)-7-hydroxy-6[(E)-(3S,4RS)-3-hydroxy-4-methyl-1-octen-6-inyl]bicyclo[3.3.0]octen-3-ylidene pentanoic acid is produced as a β-cyclodextrin inclusion compound.

What is claimed is:

1. A process comprising providing an oxidation inhibitor to provide a reduced ozone content process gas before contacting the gas with an active ingredient.

2. A process according to claim 1, wherein the oxidation inhibitor is
an inert gas atmosphere,
a closed circuit comprising synthetic air,
a metal catalyst, an irradiation device with ultraviolet light,
a heating device with temperatures of 250° C. and more and a cooling device of the process gas, and
an activated-carbon filter, through which the process gas flows.

3. A process according claim 2, wherein the activated-carbon filter has: (i) a short contact time, (ii) a minimum possible pressure drop through the filter, (iii) a hydrophobic activated carbon, and (iv) a long service life filter.

4. A process according to claim 1, wherein the active ingredient is a prostane derivative.

5. A process according to claim 4, wherein the prostane derivative is found in a wet phase.

6. A process according to claim 3, wherein the prostane derivative is 5-(E)-(1S,5S,6R)-7-hydroxy-6[(E)-(3S,4RS)-3-hydroxy-4-methyl-1-octen-6-inyl]bicyclo[3.3.0]octen-3-ylidene pentanoic acid.

7. A process according to claim 6, wherein the prostane derivative is a β-cyclodextrin inclusion compound.

8. A process according to claim 1, wherein the oxidation inhibitor is
an inert gas atmosphere,
a closed circuit comprising synthetic air,
a heating device with temperatures of at least 250° C. and a cooling device, or
an activated carbon filter.

9. A process according to claim 1, wherein the oxidation inhibitor is an activated carbon filter.

10. A process according to claim 1, wherein the active ingredient comprises
a mixture of a prostane derivative and a cyclodextrin.

11. A process according to claim 1, wherein the process gas is air.

12. A process according to claim 11, wherein the reduced ozone content of the process gas is no more than 20 µg of ozone/m$^3$ of air.

13. A process for producing a medication comprising a prostane derivative comprising:

(i) mixing of the active ingredient prostane-derivative-cyclodextrin and the adjuvants lactose and avicel in the presence of a process gas with a reduced ozone content,
(ii) pelletizing with about 20.5% water
high-speed mixing
extruding
spheronization
(iii) drying in a fluidized-bed dryer
filling
drying.

14. A process for producing a medication comprising a prostane derivative, comprising:
(i) mixing of the active ingredient iloprost-β-cyclodextrin, which bears the systematic designation 5-(E)-(1S,5S,6R)-7-hydroxy-6[(E)-(3S,4RS)-3-hydroxy-4-methyl-1-octen-6-inyl]bicyclo[3.3.0]octen-3-ylidene pentanoic acid, and the adjuvants lactose and avicel in the presence of a process gas with a reduced ozone content,
(ii) pelletizing with about 20.5% water
high-speed mixing
extruding
spheronization
(iii) drying in a fluidized-bed dryer
filling
drying.

15. A process for making a medicant comprising reducing the ozone content in air by treating the air with an oxidation inhibitor.

16. A process according to claim 15, wherein the oxidation inhibitor is
a metal catalyst,
an ultraviolet light irradiation device,
a heat device of at least 250° C. and a cooling device, or
an activated-carbon filter.

17. A process according to claim 15, wherein the oxidation inhibitor is an activated-carbon filter.

18. A process according to claim 15, wherein the reduced ozone content of the air is no more than 20 μg of ozone/m³ of air.

19. A process according to claim 15, further comprising processing an active ingredient in the presence of a reduced ozone content air.

20. A process according to claim 19, wherein the active ingredient comprises a cyclodextrin.

21. A process according to claim 19, wherein the active ingredient comprises a prostane derivative.

22. A process according to claim 19, wherein the prostane derivative is of the formula:

Formula I

Formula II wherein:

$X_1$ is a —$CH_2$—$CH_2$—; trans —CH=CH— or —C≡C—, $X_2$ is a straight-chain or branched, saturated alkylene group with 1–6 carbon atoms, $X_3$ is an —O— or —$CH_2$—, $X_4$ is a —$CH_2$— or —$[CH_2]_3$—, $X_5$ is an —H or —C≡C—$R_2$, $R_1$ is a hydrogen atom, an alkyl group with 1–6 carbon atoms, a cycloalkyl group with 5 or 6 carbon atoms or a phenyl group, $R_2$ is a straight-chain or branched-chain, saturated or unsaturated alkyl group with 1–6 carbon atoms, $R_3$ is a hydrogen atom, an acyl radical with 1–4 carbon atoms or a benzoyl radical, and $R_4$ is an —H or —$CH_3$;

wherein the —O—$R_3$ group is in α- or β-position, and its salts with physiologically compatible bases, if $R_1$ has the meaning of a hydrogen atom.

23. A process according to claim 22, wherein $X_2$ is methylene, ethylene, propylene, isopropylene, butylene, methylpropylene, ethylethylene, dimethylethylene, pentyl, methylbutylene, dimethylpropylene, ethylpropylene, methylethylethylene, hexylene, methylpentylene, dimethylbutylene, or methylethylpropylene.

24. A process according to claim 22, wherein $R^1$ is methyl, ethyl, propyl, butyl, isobutyl, tert-butyl, pentyl, neopentyl or hexyl.

25. A process according to claim 22, wherein $R^2$ is methyl, ethyl, propyl, butyl, isobutyl, tert-butyl, pentyl, hexyl, butenyl, isobutenyl, propenyl, pentenyl or hexenyl.

26. A process according to claim 22, wherein $R^3$ is acetyl, propionyl, butyryl or isobutyryl.

27. A process for making a medicant comprising processing an active ingredient in a reduced ozone atmosphere.

28. A process according to claim 27, wherein the reduced ozone atmosphere is an inert gas atmosphere.

29. A process for a prostane derivative, comprising providing a process gas with a reduced ozone content by a means for oxidation inhibition.

* * * * *